(12) United States Patent
Irie et al.

(10) Patent No.: US 7,423,174 B2
(45) Date of Patent: Sep. 9, 2008

(54) METHOD OF SEPARATING ACID

(75) Inventors: Masaki Irie, Settsu (JP); Masahiro Kondou, Settsu (JP)

(73) Assignee: Daikin Industries, Ltd., Osaka-Shi (JP)

( * ) Notice: Subject to any disclaimer, the term of this patent is extended or adjusted under 35 U.S.C. 154(b) by 549 days.

(21) Appl. No.: 10/477,198

(22) PCT Filed: May 30, 2002

(86) PCT No.: PCT/JP02/05312

§ 371 (c)(1), (2), (4) Date: Nov. 17, 2003

(87) PCT Pub. No.: WO02/098792

PCT Pub. Date: Dec. 12, 2002

(65) Prior Publication Data

US 2004/0158100 A1 Aug. 12, 2004

(30) Foreign Application Priority Data

Jun. 5, 2001 (JP) .............................. 2001-169187
Dec. 27, 2001 (JP) .............................. 2001-396680

(51) Int. Cl.
*C01B 31/00* (2006.01)
*C07C 51/64* (2006.01)
*C08F 226/06* (2006.01)

(52) U.S. Cl. ........................ 562/866; 562/840; 562/849; 562/856

(58) Field of Classification Search ................. 562/840, 562/849, 856, 866
See application file for complete search history.

(56) References Cited

U.S. PATENT DOCUMENTS 2,645,649 A * 7/1953 Hoffman ...................... 554/30
2,836,622 A 5/1958 Tullock ...................... 260/544

(Continued)

FOREIGN PATENT DOCUMENTS

GB 1007288 9/1963

(Continued)

OTHER PUBLICATIONS

Cao et al. Applied and environmental microbiology 1996, vol. 62, No. 8, pp. 2926-2931.*

(Continued)

*Primary Examiner*—Yvonne Eyler
*Assistant Examiner*—Yevegeny Valenrod
(74) *Attorney, Agent, or Firm*—Kratz, Quintos & Hanson, LLP

(57) ABSTRACT

The present invention provides a process for selectively separating HF and like acids present along with water-unstable organic acid fluorides. In particular, the invention provides a process for separating an acid from a system in which the acid and an organic acid fluoride are present, the organic acid fluoride being represented by formula (I):

RCOF (I)

wherein R is a fluorine atom; a $C_{1-20}$ linear, branched or cyclic alkyl or halogenated alkyl group that may contain a heteroatom; or a $C_{6-20}$ aryl or halogenated aryl group that may contain a heteroatom; the process comprising using as a deacidifying agent an aromatic heterocyclic compound having a boiling point of at least 50° C. and having one or more nitrogen atoms as heteroatom.

7 Claims, 2 Drawing Sheets

U.S. PATENT DOCUMENTS

| | | | |
|---|---|---|---|
| 4,629,610 A | 12/1986 | Friese et al. | 423/240 |
| 4,640,831 A | 2/1987 | DeVries | 423/481 |
| 5,360,928 A * | 11/1994 | Carpino et al. | 562/849 |
| 5,942,536 A * | 8/1999 | Fritz et al. | 514/414 |
| 5,980,753 A | 11/1999 | Itano et al. | 210/670 |

FOREIGN PATENT DOCUMENTS

| | | |
|---|---|---|
| JP | 49-96996 | 9/1974 |
| JP | 54-158396 | 12/1979 |
| JP | 57-164991 | 10/1982 |
| JP | 58-192852 | 11/1983 |
| JP | 59-39705 | 3/1984 |
| JP | 04-227706 | 8/1992 |
| JP | 4-227706 | 8/1992 |
| JP | 5-213812 | 8/1993 |
| JP | 8-231462 | 9/1996 |
| JP | 11-116216 | 4/1999 |
| JP | 2000-301006 | 10/2000 |
| WO | WO 96/19425 | 6/1966 |
| WO | WO 02/098792 | 12/2002 |

OTHER PUBLICATIONS

Olah et al; "Poly-4-yinylpyridinium Poly (Hydrogen Fluoride): A Solid Hydrogen Fluoride Equivalent Reagent"; *Synthesis*, 1993; pp. 693-699.

International Search Report dated Sep. 3, 2002.

European Office Action dated May 15, 2008.

* cited by examiner

METHOD OF SEPARATING ACID

TECHNICAL FIELD

The present invention relates to a process for selectively removing HF, HCl, HBr and like acids present along with organic acid fluorides (RCOF) that are unstable to water, ammonia, etc. More particularly, the invention is directed to a process useful for efficiently removing acids without decomposing $COF_2$, $CF_3COF$ and the like.

BACKGROUND OF THE INVENTION

Organic acid fluorides are used as starting materials for a variety of fluorine-containing organic compounds, especially for the perfluorovinyl ethers that are important as comonomers constituting polymers such as resins and elastomers. For example, an oligomerization reaction with hexafluoropropylene oxide (HFPO) as represented by the formula below can be considered as an important reaction.

$$RCOF + n(HFPO) \rightarrow RCF_2O(CF(CF_3)CF_2O)_{n-1}CF(CF_3)COF$$

The product of this reaction is also important as a precursor of the aforementioned perfluorovinyl ethers, and as a starting material for producing fluorine-containing ethers, fluorine-containing alcohols, etc. It is known to conduct this reaction in an aprotic polar organic solvent in the presence of a catalyst such as alkali metal halides, alkyl ureas, quaternary ammonium halides or the like. However, when the starting material contains even small amounts of hydrogen fluoride, hydrogen chloride or like acidic gases, water, carboxylic acid, or the like, a phenomenon occurs in which expensive catalysts are deactivated. The presence of water causes an RCOF— type compound to decompose into RCOOH and HF. Therefore, insufficient drying through carelessness may well generate HF, so that the catalyst may be easily inactivated. For instance, $COF_2$ is generated as a by-product in producing hexafluoropropylene oxide by oxidizing hexafluoropropylene with oxygen, and HF is present along with this $COF_2$. Therefore, such $COF_2$, when used as a starting material in the aforementioned oligomerization reaction, poses a problem of enzymatic deactivation due to the presence of HF. Given the above circumstance, a demand has existed for the development of a process for removing the acids present in RCOF in order to prevent catalyst deactivation.

Among organic acid fluorides, $COF_2$ is a hopeful candidate for an etching or chamber cleaning gas for use in semiconductor production free from the concern of any contribution to global warming. However, as described above, acids are usually present when $COF_2$ is produced, thereby posing problems such as corroding equipment and transportation containers due to the presence of the acids. For this reason, the development of a process for acid removal is also strongly desired.

Because, as mentioned above, RCOF is unstable with respect to water, deacidifying agents such as $Al_2O_3$, $SiO_2$ and like that produce water by reaction with HF cannot be used, not to mention conventional aqueous alkaline solutions. Furthermore, deacidifying agents containing ammonia or primary or secondary amines form amides with RCOF and thereby bind starting materials, making the use of such deacidifying agents impossible in the aforementioned oligomerization reaction.

In contrast, sodium fluoride, potassium fluoride and the like are known deacidifying agents that do not generate water even after adsorbing HF. However, they have disadvantages, such as poor deacidifying efficiency requiring large-scale treatment devices to remove HF to the degree that the deacidified RCOF can withstand the oligomerization reaction, and significant energy consumption requiring high temperatures of 350° C. or more to recycle these deacidifying agents by thermally desorbing the adsorbed acids.

Rectification is an example of a process that does not require the use of a deacidifying agent. However, despite the fact that $COF_2$ and HF, for example, have a boiling point difference of over 100° C., it is not easy to separate $COF_2$ and HF through conventional rectification processes, making the conventional processes inappropriate and requiring a complex process.

As described above, there is currently no useful process for removing acids present alongside RCOF to prevent catalyst deactivation or the corrosion of equipment and transportation containers when RCOF is used as a gas employed in semiconductor production.

DISCLOSURE OF THE INVENTION

The present invention provides a process for selectively removing HF, HCl, HBr and like acids present along with organic acid fluorides that are especially unstable to water; provides organic acid fluorides that are obtained through the process and that have concomitant acids in a concentration of 100 mass ppm or less; and provides a process for recycling the deacidifying agents used in the process for removing acids. More particularly, the invention provides a process useful for effectively removing acids without decomposing $COF_2$, $CF_3COF$ and the like.

The inventors conducted extensive research in view of the prior art problems described above and found that acids present along with organic acid fluorides can be separated, without decomposing the organic acid fluorides, by using as deacidifying agents aromatic heterocyclic compounds having a boiling point of at least 50° C. and having one or more nitrogen atoms as heteroatom, and that organic acid fluorides having concomitant acids in a concentration of 100 mass ppm or less can be produced through this separation. Furthermore, the inventors also found that deacidifying agents used in the acid separation can be readily recycled by thermal or alkaline desorption.

In particular, the present invention provides an organic acid fluoride, a process for separating an acid, and a process for recycling a deacidifying agent.

Item 1. A process for separating an acid from a system in which the acid and an organic acid fluoride are present, the organic acid fluoride being represented by formula (I):

$$RCOF \quad (I)$$

wherein R is a fluorine atom; a $C_{1-20}$ linear, branched or cyclic alkyl or halogenated alkyl group that may contain a heteroatom; or a $C_{6-20}$ aryl or halogenated aryl group that may contain heteroatom;

the process comprising using as a deacidifying agent an aromatic heterocyclic compound having a boiling point of at least 50° C. and having one or more nitrogen atoms as heteroatom.

Item 2. A process for separating an acid according to Item 1, wherein the acid is at least one member selected from the group consisting of HF, HCl and HBr.

Item 3. A process for separating an acid according to Item 1, wherein the acid is HF.

Item 4. A process for separating an acid according to Item 1, wherein the deacidifying agent is a polymer that has one or more aromatic heterocyclic groups having one or more nitrogen atoms as heteroatom.

Item 5. A process for separating an acid according to Item 1, wherein the deacidifying agent is a polymer having pyridyl group.

Item 6. A process for separating an acid according to Item 1, wherein the deacidifying agent is at least one polymer selected from the group consisting of poly(4-vinylpyridine), poly(2-vinylpyridine), and copolymers prepared by copolymerizing vinylpyridine with styrene, divinylbenzene or butyl methacrylate.

Item 7. A process for separating an acid according to Item 1, wherein the organic acid fluoride is at least one member selected from the group consisting of $COF_2$, $CH_3COF$, $CF_3COF$, $C_2H_5COF$, $C_2F_5COF$, $C_3H_7COF$, $C_3F_7COF$, $CF_3OCF(CF_3)COF$, $CF_3OCF_2COF$ and $C_6H_5COF$.

Item 8. A process for separating an acid according to Item 1, wherein the organic acid fluoride is $COF_2$.

Item 9. A process for separating an acid according to Item 1, wherein the system in which an organic acid fluoride and an acid are present is a system in which an organic acid fluoride is produced.

Item 10. A process for separating an acid according to Item 1, wherein the system in which an organic acid fluoride and an acid are present is a system in which carbonyl fluoride and HF that are obtained as by-products in the production of hexafluoropropylene oxide by oxidizing hexafluoropropylene with oxygen are present.

Item 11. An organic acid fluoride obtained according to the process of Item 1 having a concomitant acid in a concentration of 100 mass ppm or less.

Item 12. $COF_2$ obtained according to the process of Item 1 having a concomitant acid in a concentration of 100 mass ppm or less.

Item 13. A process for recycling a polymer having pyridyl group that is used as a deacidifying agent, by thermal desorption or alkaline desorption.

The present invention is suitable for use as a treatment method in cases where it is not preferable for a gaseous or liquid organic acid fluoride (RCOF) to contain hydrofluoric acid or like protonic acids. In the formula, R is a fluorine atom; a $C_{1-20}$ linear, branched or cyclic alkyl or halogenated alkyl group that may contain a heteroatom; or a $C_{6-20}$ aryl or halogenated aryl group that may contain a heteroatom. Fluorine is preferable as the halogen of the halogenated alkyl or aryl group. Examples of organic acid fluorides (RCOF) wherein R represents a $C_{1-20}$ alkyl or halogenated alkyl group having a heteroatom include $CF_3OCF(CF_3)COF$, $CF_3OCF_2COF$ and compounds represented by following formula (II):

$$R^1-X-CR^2-COF \hspace{2em} (II)$$

wherein $R^1$ is a $C_{1-19}$ linear, branched or cyclic alkyl or halogenated alkyl group; $R^2$ represents a hydrogen atom, halogen atom (preferably a fluorine atom) or a $C_{1-5}$ alkyl or halogenated alkyl group; and X is an oxygen atom or an NF group.

Examples of preferable organic acid fluorides include $COF_2$, $CH_3COF$, $CF_3COF$, $C_2H_5COF$, $C_2F_5COF$, $C_3H_7COF$, $C_3F_7COF$, $CF_3OCF(CF_3)COF$, $CF_3OCF_2COF$, $C_6H_5COF$ and the like. More preferable are $COF_2$, $CF_3COF$, $C_3F_7COF$, etc. As organic acid fluorides, liquid and gaseous compounds are herein usable.

In the present invention, the system in which an organic acid fluoride and an acid are present is not limited insofar as $COF_2$, $CH_3COF$ or similar organic acid fluoride, and HF or similar acid can co-exist. Examples include systems in which an organic acid fluoride and HF are present due to the decomposition of RCOF produced in the production of an organic acid fluoride to RCOOH and HF caused by the reaction with water (when the compound produced in the production of an organic acid fluoride is $COF_2$, this $COF_2$ reacts with water and decomposes to $CO_2$ and HF); systems in which an organic acid fluoride and HCl or HBr are present due to the reaction of an organic acid chloride with HF or the reaction of an organic acid bromide with HF, as may occur in the production of organic acid fluorides, and like systems.

Specific examples include systems in which carbonyl fluoride and HF that are obtained as by-products in the production of hexafluoropropylene oxide by oxidizing hexafluoropropylene with oxygen are present.

The acids herein are not limited. Specific examples include HF, HCl, HBr and the like. HF is preferable.

Deacidifying agents used in the present invention are aromatic heterocyclic compounds that have a boiling point of at least 50° C. and have one or more nitrogen atoms as heteroatom.

In such aromatic heterocyclic compounds having one or more nitrogen atoms as heteroatom, at least one element constituting the aromatic heterocyclic ring is nitrogen. Examples are imidazole, pyridine, quinoline, acridine, phenanthridine, pyridazine, pyrimidine, pyrazine, cinnoline, phthalazine, quinazoline, quinoxaline, phenazine, triazole, triazine, etc.

The aforementioned aromatic heterocyclic compounds include polymers that have one or more aromatic heterocyclic groups having one or more nitrogen atoms as heteroatom. Such polymers include anion-exchange resins that have such aromatic heterocyclic groups having one or more nitrogen atoms as heteroatom as ion-exchange groups. Examples of ion-exchange groups include pyridyl, imidazole, quinoline, acridine, phenanthridine, pyridazine, pyrimidine, pyrazine, cinnoline, phthalazine, quinazoline, quinoxaline, phenazine, triazole, triazine, and like groups.

Examples of ion-exchange resins having such ion-exchange groups are homopolymers such as poly(4-vinylpyridine), poly(2-vinylpyridine) and the like, and polymers having a pyridyl group such as copolymers obtained by copolymerizing vinylpyridine with styrene, divinylbenzene, butyl methacrylate, or the like. Preferable are polymers having a pyridyl group, and more preferable are copolymers of vinylpyridine and divinylbenzene.

The aforementioned deacidifying agents are introduced into the systems in which an organic acid fluoride and an acid are present to separate the acid. For example, in a system in which an organic acid fluoride and an acid are present, gas-liquid contact is carried out at a temperature of −10 to 50° C., preferably 0 to 40° C., using the deacidifying agent, and then the deacidifying agent mixed in the reaction product is isolated by distillation.

When the deacidifying agent is solid, although the contacting method is not limited, deacidification can be conducted by flowing RCOF, preferably at a constant rate, through a reaction tube charged with the deacidifying agent. Although variable depending on the flow rate, a relatively short contact time is satisfactory. However, at least 20 seconds of contact time is preferable to obtain sufficient efficiency. Reaction tube materials are not limited insofar as they are acid resistant. Stainless steel, resins and glass can be used, although glass vessels are not suitable for use in deacidification of HF. When heated to thermally recycle the deacidifying agents, a stainless-steel reaction tube is preferable due to its heat resistance.

The amount of deacidifying agent can be suitably selected at will. When gaseous fluid is brought into contact in a reaction tube, although the amount of deacidifying agent can be suitably selected, but it is preferably such that the length of a reaction tube should be no more than 20 cm to avoid excessive pressure loss.

Deacidification is conducted in the range of −10 to 120° C., preferably 0 to 80° C. When temperature exceeds 120° C., the desired deacidification effect may not be obtained since adsorbed protonic acids may be desorbed.

While the deacidification treatment can be conducted under reduced, atmospheric or increased pressures, atmospheric or increased pressures are preferable for efficacious contact.

Although protonic acids may be present along with organic acid fluorides in varying concentrations, the preferable concentration is 30 mol % or less since excessive concentrations cause excessive heat generation upon adsorption. When a sufficient contact time is available, organic acid fluorides having concomitant protonic acids of any concentration can be deacidified to an acid concentration of about 10 ppm.

The adsorption amount is described in "Synthesis" (George A. Olah, Xing-Ya Li, Qi Wang, G. K. Surya Prakash, 1993, pp. 693-699). The amount of HF present along with the organic acid fluoride is preferably no more than 3 moles per mole of the pyridyl groups of a deacidifying agent. The amount of protonic acid other than HF is preferably in equimolar or less.

When a deacidifying treatment is conducted using the aforementioned organic acid fluoride, acid and deacidifying agent in combination, by contacting the organic acid fluoride with the deacidifying agent, one or more nitrogen atoms in the deacidifying agent acts as a base and the protonic acid can be selectively removed without decomposing the organic acid fluoride. Furthermore, when an ion-exchange resin is used as the deacidifying agent, the deacidifying agent can be readily recycled after deacidification by heating or an alkaline aqueous solution treatment.

As an ion-exchange resin recycling process, thermal desorption is preferable over alkaline desorption because drying is required after alkaline desorption. In thermal desorption, recycling can be achieved simply by heating the deacidifying agent to 100 to 165° C., preferably 120 to 155° C. Temperatures exceeding 165° C. are not preferable due to reduced readsorbing capabilities. The heating time is suitably selected according to the type and amount of the deacidifying agent used and the acid adsorbed by the deacidifying agent. In alkaline desorption, since ion-exchange groups such as pyridyl and other groups of the deacidifying agent become protonic acid salts, the deacidifying agent can be readily recycled by contacting it with stronger alkalies, such as aqueous NaOH, aqueous KOH and the like.

The organic acid fluoride obtained according to the process for separating an acid of the invention is at least one fluoride selected from the group consisting of $COF_2$, $CH_3COF$, $CF_3COF$, $C_2H_5COF$, $C_2F_5COF$, $C_3H_7COF$, $C_3F_7COF$, $CF_3OCF(CF_3)COF$, $CF_3OCF_2COF$ and $C_6H_5COF$. Preferable is an organic acid fluoride having concomitant acids in a concentration of 100 mass ppm or less. The more preferable organic acid fluoride is $COF_2$.

The term FIC stands for flow indicator control, controlling the gas flow at a constant rate through the use of a mass flow controller.

BEST MODE FOR CARRYING OUT THE INVENTION

Examples are given below to illustrate the invention in more detail, but the scope of the invention is not limited to these examples.

EXAMPLE 1

Figure 1:
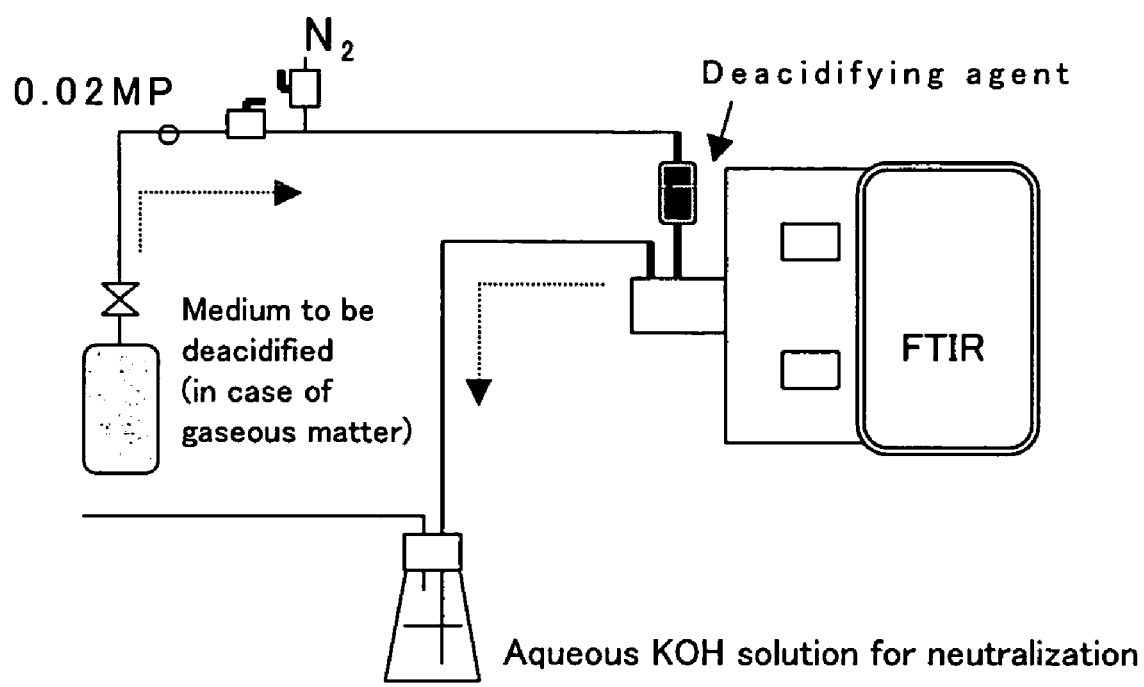
FIG. 1 shows the reactor used in Example 1.

Using the device shown in FIG. 1, the concentration of hydrogen fluoride in the medium was measured by an FTIR spectrometer (IGA-2000, product of Otsuka Electronics, Co., Ltd.). The IR cell material was nickel and the cell had a length of 10 cm. A liquid-nitrogen-cooled-type MCT was used as a detector.

$COF_2$ gas was used as the gas medium and 4-vinylpyridine/ 2% divinylbenzene copolymer (particle size: 60 mesh, product of Acros Organics) was used as the deacidifying agent. The deacidifying agent was used in an amount of 3.2 g (about 5.4 cc), charged into a 3/8-inch stainless-steel tube (charged portion length: 12 cm) and heated for 2 hours in a vacuum at a temperature of 150° C. as a predrying step. After the stainless-steel tube was cooled to room temperature, $COF_2$ gas containing HF in an amount of 1,050 ppm (mol) was introduced at a rate of 50 to 70 cc/min into the FTIR cell through the deacidifying agent. The results of the measurement showed that the concentration of HF was reduced to 2 to 11 ppm. Even when the gas was kept flowing for an additional 50 minutes or so, the concentration was maintained at 11 ppm or less.

EXAMPLE 2

Figure 2:
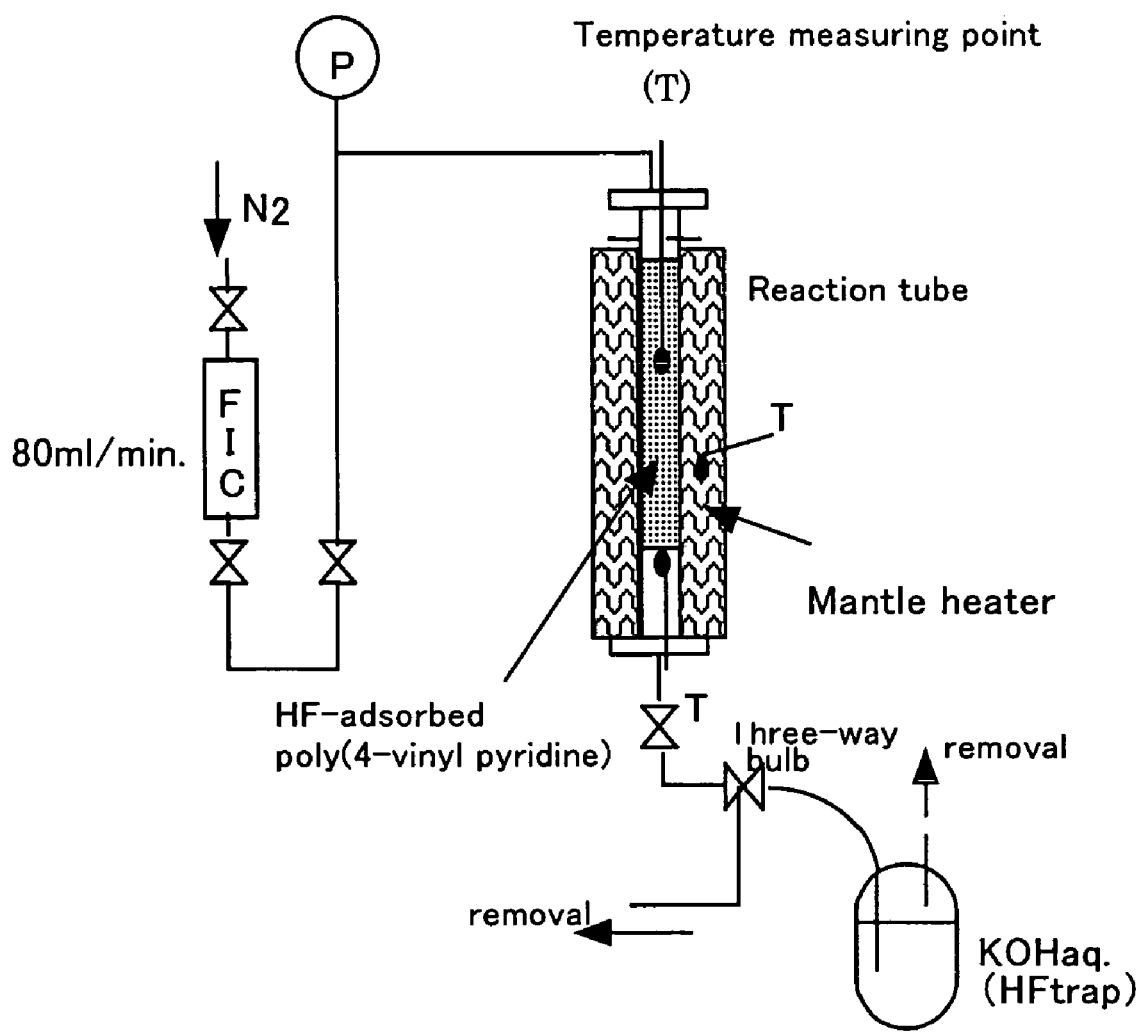
FIG. 2 shows the reactor used in Example 2.

A deacidifying agent recycling treatment was conducted over a period of 10 hours by charging the reaction tube (diameter: 2 cm, length: 25 cm) of the device shown in FIG. 2 with a solution (21.9 g in total) in which 7.5 g of HF was adsorbed on 14.4 g of 4-vinylpyridine/2% divinylbenzene copolymer; flowing nitrogen gas through the device (reaction tube???) at a rate of 80 ml/min; and heating the device until the external temperature reached 155° C. and the internal temperature reached 130 to 150° C. HF was trapped by an aqueous potassium hydroxide solution provided at the outlet port of the nitrogen gas. The amount of HF recovered was 6.15 g based on the measurement of the weight increase of the solution. The polymer was recovered in an amount of 15.6 g, and this recovered polymer could be reused as if new.

COMPARATIVE EXAMPLE 1

The concentration of HF was measured in the same manner as in Example 1 except that the 4-vinylpyridine/2% divinylbenzene copolymer used as a deacidifying agent was replaced with 6.5 g of sodium fluoride (charged portion length: 15 cm). The result showed that the concentration was in a range of 200 to 300 ppm.

INDUSTRIAL APPLICABILITY

According to the present invention, acids can be separated from a system in which an organic acid fluoride (RCOF) and an acid are present without decomposing the organic acid fluoride. In addition, when an ion-exchange resin is used as a deacidifying agent, the deacidifying agent used for acid separation can be readily recycled by thermal or alkaline desorption. Therefore, through the use of the present invention, acids, which are useless and harmful in the oligomerization of an organic acid fluoride and hexafluoropropylene oxide, can be removed in a pretreatment with the deacidifying agent. Furthermore, since deacidifying agents can be readily recycled by heating them, the present invention can be used as an inexpensive deacidifying process as it does not require the replacement of acidifying agents.

Moreover, the present invention provides an organic acid fluoride usable in semiconductor production as an etching gas and chamber cleaning gas free from the concern of any contribution to global warming, because corrosion of production equipment and transportation containers and other problems caused by the presence of acids are alleviated by the removal of acids.

The invention claimed is:

1. A process for separating an acid from a system comprising the acid and an organic acid fluoride;
   the organic acid fluoride being represented by formula (I):

RCOF   (I)

wherein R is a fluorine atom; a $C_{1-20}$ linear, branched or cyclic alkyl or halogenated alkyl group that may contain a heteroatom; or a $C_{6-20}$ aryl or halogenated aryl group that may contain a heteroatom;
   the acid being HF;
   the process comprising using as a deacidifying agent a polymer that has one or more aromatic heterocyclic groups having one or more nitrogen atoms as heteroatom having a boiling point of at least 50° C. and having one or more nitrogen atoms as heteroatom; and the resulting organic acid fluoride having a concomitant acid in a concentration of 100 mass ppm or less.

2. A process for separating an acid according to claim 1, wherein the deacidifying agent is a polymer having pyridyl group.

3. A process for separating an acid according to claim 1, wherein the deacidifying agent is at least one polymer selected from the group consisting of poly(4-vinylpyridine), poly(2-vinylpyridine), and copolymers prepared by copolymerizing vinylpyridine with styrene, divinylbenzene or butyl methacrylate.

4. A process for separating an acid from a system comprising the acid and an organic acid fluoride;
   the organic acid fluoride being represented by formula (I):

RCOF   (I)

wherein R is a fluorine atom; a $C_{1-20}$ linear, branched or cyclic alkyl or halogenated alkyl group that may contain a heteroatom; or a $C_{6-20}$ aryl or halogenated aryl group that may contain a heteroatom;
   the process comprising using as a deacidifying agent an aromatic heterocyclic compound having a boiling point of at least 50° C. and having one or more nitrogen atoms as heteroatom;
   wherein the organic acid fluoride is at least one member selected from the group consisting of $COF_2$, $CH_3COF$, $CF_3COF$, $C_2H_5COF$, $C_2F_5COF$, $C_3H_7COF$, $C_3F_7COF$, $CF_3OCF(CF_3)COF$, $CF_3OCF_2COF$ and $C_6H_5COF$.

5. A process for separating an acid according to claim 4, wherein the organic acid fluoride is $COF_2$.

6. A process for separating an acid according to claim 1, wherein an organic acid fluoride is produced in the system.

7. A process for separating an acid according to claim 1, wherein carbonyl fluoride and HF, which are obtained as by-products in the production of hexafluoropropylene oxide by oxidizing hexafluoropropylene with oxygen, are present in the system.

* * * * *